United States Patent
Al-deen Rizq

(10) Patent No.: US 12,360,031 B2
(45) Date of Patent: Jul. 15, 2025

(54) ONLINE PARTICLES COUNT MONITORING SYSTEM AND SEAWATER INJECTION SYSTEM COMPRISING THE SAME

(71) Applicant: Saudi Arabian Oil Company, Dhahran (SA)

(72) Inventor: Ahmad Noor Al-deen Rizq, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 285 days.

(21) Appl. No.: 18/152,293

(22) Filed: Jan. 10, 2023

(65) Prior Publication Data
US 2024/0230502 A1 Jul. 11, 2024

(51) Int. Cl.
*G01N 15/06* (2024.01)
*E21B 21/08* (2006.01)
*E21B 49/08* (2006.01)
*G01N 33/28* (2006.01)

(52) U.S. Cl.
CPC ......... *G01N 15/0643* (2013.01); *E21B 21/08* (2013.01); *E21B 49/0875* (2020.05); *G01N 33/2823* (2013.01)

(58) Field of Classification Search
CPC ............ G01N 15/0643; G01N 33/2823; E21B 49/0875; E21B 21/08
See application file for complete search history.

(56) References Cited

U.S. PATENT DOCUMENTS

| | | | | |
|---|---|---|---|---|
| 7,689,368 B2* | 3/2010 | Douglas | ........... | G01N 35/00722 702/33 |
| 2020/0139276 A1* | 5/2020 | Wetherill | ........... | G01N 15/0806 |
| 2020/0368651 A1* | 11/2020 | Besnier-Amogu | ..... | B01D 33/50 |

OTHER PUBLICATIONS

Hansen et al., "Online Quality Measurements of Total Suspended Solids for Offshore Reinjection: A Review Study", Energies, vol. 14, No. 967, pp. 24-48, 2021.
Shaddel et al., "Core Flood Studies to Evaluate Efficiency of Oil Recovery by Low Salinity Water Flooding as a Secondary Recovery Process", Journal of Petroleum Science and Technology, vol. 4, No. 1, pp. 47-56, 2014.

* cited by examiner

*Primary Examiner* — Kristina M Deherrera
*Assistant Examiner* — Jean F Morello
(74) *Attorney, Agent, or Firm* — DINSMORE & SHOHL LLP

(57) ABSTRACT

A seawater injection system comprises a primary seawater supply line, a diverted seawater sampling line, and an online particles count monitoring system. The online particles count monitoring system is coupled to the primary seawater supply line through the diverted seawater sampling line such that a portion of a primary flow of seawater can be diverted to the online particles count monitoring system. The online particles count monitoring system comprises a diverted seawater inlet, a core plug assembly, a diverted seawater outlet, and an inlet pressure monitoring station between the core plug assembly and the diverted seawater inlet. The core plug assembly comprises a core plug and a removable particle filter. The inlet pressure monitoring station generates a particles count signal based on fluid pressure in diverted seawater moving through the diverted seawater sampling line in a downstream direction of the core plug and the removable particle filter.

20 Claims, 1 Drawing Sheet

ONLINE PARTICLES COUNT MONITORING SYSTEM AND SEAWATER INJECTION SYSTEM COMPRISING THE SAME

BACKGROUND

The present disclosure relates to an online particles count monitoring system and seawater injection system comprising the online particles count monitoring system for monitoring particles count in a sampling line.

BRIEF SUMMARY

According to the subject matter of the present disclosure, in oil and gas drilling, wellbore stimulation is a common treatment performed in subsurface formations to enhance or restore the productivity of oil and gas from a hydrocarbon-containing well and associated wellbore. Hydraulic fracturing may be one method of wellbore stimulation. In hydraulic fracturing, pressure in the wellbore is increased by injecting an injection fluid until a conductive fracture is created that helps enhance the production of oil and gas from the subsurface formation. The injection fluid, produced from seawater, is treated to contain particles to have a certain quality.

In accordance with one embodiment of the present disclosure, a seawater injection system comprising a primary seawater supply line, a diverted seawater sampling line, and an online particles count monitoring system is provided. The online particles count monitoring system is fluidly coupled to the primary seawater supply line through the diverted seawater sampling line such that a portion of a primary flow of seawater moving in a downstream direction through the primary seawater supply line can be diverted to the online particles count monitoring system through the diverted seawater sampling line. The online particles count monitoring system comprises a diverted seawater inlet, a core plug assembly downstream of the diverted seawater inlet, a diverted seawater outlet downstream of the core plug assembly, and an inlet pressure monitoring station upstream of the core plug assembly and downstream of the diverted seawater inlet. The core plug assembly comprises a core plug and a removable particle filter arranged upstream of the core plug. The diverted seawater inlet is fluidly coupled to the diverted seawater outlet through the core plug assembly such that diverted seawater moving in a downstream direction through the diverted seawater inlet can be directed to the diverted seawater outlet through the removable particle filter and the core plug of the core plug assembly. The core plug comprises a core plug inlet face and the removable particle filter is supported by the core plug inlet face, extends across a majority of the core plug inlet face, and is characterized by a pore size rating of at least about 0.45 microns. The core plug inlet face and the removable particle filter are oriented to directly obstruct the flow of diverted seawater such that particles collected by the removable particle filter will increase fluid pressure in diverted seawater moving through the diverted seawater sampling line at a constant flow rate. The inlet pressure monitoring station generates a particles count signal based on fluid pressure in diverted seawater moving through the diverted seawater sampling line in a downstream direction of the core plug inlet face and the removable particle filter.

In accordance with another embodiment of the present disclosure, an online particles count monitoring system is provided. The online particles monitoring system comprises a diverted seawater inlet, and a core plug assembly downstream of the diverted seawater inlet. The core plug assembly comprises a core plug and a removable particle filter arranged upstream of the core plug. The online particles monitoring system further comprises a diverted seawater outlet downstream of the core plug assembly, and an inlet pressure monitoring station upstream of the core plug assembly and downstream of the diverted seawater inlet. The diverted seawater inlet is fluidly coupled to the diverted seawater outlet through the core plug assembly such that diverted seawater moving in a downstream direction through the diverted seawater inlet can be directed to the diverted seawater outlet through the removable particle filter and the core plug of the core plug assembly. The core plug comprises a core plug inlet face and the removable particle filter is supported by the core plug inlet face, extends across a majority of the core plug inlet face, and is characterized by a pore size rating of at least about 0.45 microns. The core plug inlet face of the core plug and the removable particle filter are oriented to directly obstruct the flow of diverted seawater such that particles collected by the removable particle filter will increase fluid pressure in diverted seawater moving through a diverted seawater sampling line that is fluidly coupled to the online particles count monitoring system, at a constant flow rate. The inlet pressure monitoring station generates a particles count signal based on fluid pressure in diverted seawater moving through the diverted seawater sampling line that is fluidly coupled to the online particles count monitoring system, in a downstream direction of the core plug inlet face and the removable particle filter.

In accordance with yet another embodiment of the present disclosure, an online method of monitoring particle count in a seawater injection system comprising a primary seawater supply line, a diverted seawater sampling line, and an online particles count monitoring system is provided. The online particles count monitoring system is fluidly coupled to the primary seawater supply line through the diverted seawater sampling line. The online particles count monitoring system comprises a diverted seawater inlet, a core plug assembly downstream of the diverted seawater inlet, a diverted seawater outlet downstream of the core plug assembly, and an inlet pressure monitoring station upstream of the core plug assembly and downstream of the diverted seawater inlet. The core plug assembly comprises a core plug and a removable particle filter arranged upstream of the core plug. The diverted seawater inlet is fluidly coupled to the diverted seawater outlet through the core plug assembly such that diverted seawater moving in a downstream direction through the diverted seawater inlet can be directed to the diverted seawater outlet through the removable particle filter and the core plug of the core plug assembly. The core plug comprises a core plug inlet face and the removable particle filter is supported by the core plug inlet face, extends across a majority of the core plug inlet face, and is characterized by a pore size rating of at least about 0.45 microns. The core plug inlet face of the core plug and the removable particle filter are oriented to directly obstruct the flow of diverted seawater. The online method comprises diverting a portion of a primary flow of seawater moving in a downstream direction through the primary seawater supply line to the online particles count monitoring system through the diverted seawater sampling line, maintaining a constant flow rate in the diverted seawater sampling line such that particles collected by the removable particle filter will increase fluid pressure in diverted seawater moving through the diverted seawater sampling line, and generating, by the inlet pressure monitoring station, a particles count signal based on fluid pressure in diverted seawater moving downstream through the diverted seawater sampling line in a downstream direction of the core plug inlet face and the removable particle filter.

Although the concepts of the present disclosure are described herein with primary reference to seawater injection system for oil and gas drilling, it is contemplated that the concepts will enjoy applicability to any fluid injection system. For example, and not by way of limitation, it is contemplated that the concepts of the present disclosure will enjoy applicability to an online particles count monitoring system for any fluid injection system.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

Figure 1:
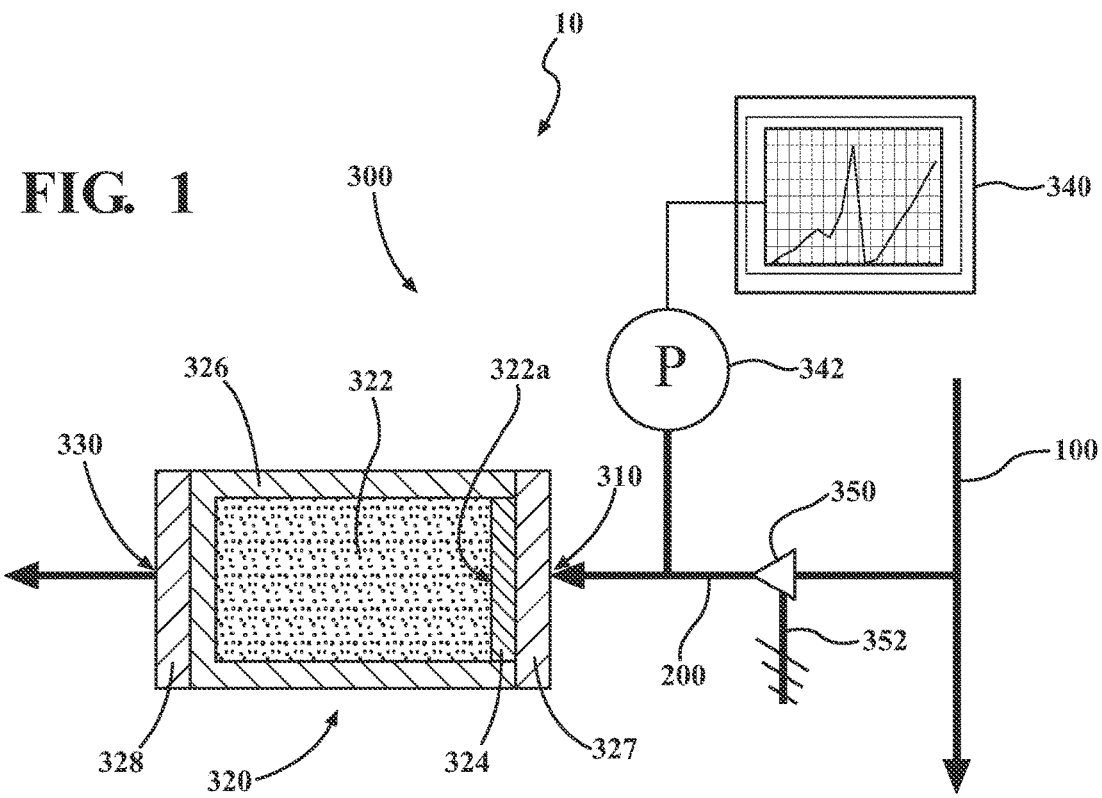
FIG. 1 is an illustrative drawing of a seawater injection system according to one or more embodiments herein.

Referring initially to FIG. 1, a seawater injection system 10 according to one embodiment of the present disclosure comprises a primary seawater supply line 100, a diverted seawater sampling line 200, and an online particles count monitoring system 300. The online particles count monitoring system 300 is fluidly coupled to the primary seawater supply line 100 through the diverted seawater sampling line 200 such that a portion of a primary flow of seawater moving in a downstream direction through the primary seawater supply line 100 can be diverted to the online particles count monitoring system 300 through the diverted seawater sampling line 200.

In embodiments, the diverted seawater sampling line 200 is configured such that no more than approximately 5% of the primary flow of seawater is diverted from the primary seawater supply line 100. As will be appreciated by those familiar with seawater injection system, and fluid handling systems in general, the primary flow of seawater can be diverted in any of a variety of conventional or yet-to-be developed ways including, for example, by merely providing a seawater diversion port and valve along the primary seawater supply line In embodiments, the seawater injection system 10 may further comprise a diverted seawater sampling line controller that controls the diverted seawater sampling line to maintain a constant flow rate in the diverted seawater sampling line. For example, the flow rate is maintained between 0.5 l/hr to 10 l/hr.

The online particles count monitoring system 300 comprises a diverted seawater inlet 310, a core plug assembly 320 downstream of the diverted seawater inlet 310, a diverted seawater outlet 330 downstream of the core plug assembly 320, and an inlet pressure monitoring station 340 upstream of the core plug assembly 320 and downstream of the diverted seawater inlet 310.

The core plug assembly 320 comprises a core plug 322 and a removable particle filter 324 arranged upstream of the core plug 322. The diverted seawater inlet 310 is fluidly coupled to the diverted seawater outlet 330 through the core plug assembly 320 such that diverted seawater moving in a downstream direction through the diverted seawater inlet 310 can be directed to the diverted seawater outlet 330 through the removable particle filter 324 and the core plug 322 of the core plug assembly 320. It is contemplated that the core plug 322 can be selected from any of a variety of existing or yet-to-be developed core plug materials, such as those commonly used in core flood systems, and may be provided in a variety of sizes. For example, and not by way of limitation, the surface area of the inlet face of the core plug 322 may be between approximately 10 cm$^2$ and approximately 32 cm$^2$, and contemplated core plug materials include glass, Teflon, Chromium, or combinations thereof. It is also contemplated that the core plug 322 and the entire core plug assembly 320 may be constructed from anti-corrosive materials, such as glass, Teflon, Chromium, or combinations thereof. In embodiments, the core plug assembly 320 further comprises a core plug holder 326, an inlet end cap 327 coupled to the diverted seawater inlet 310, and an outlet end cap 328 coupled to the diverted seawater outlet 330. The core plug holder 326 and the inlet end cap 327 may be collectively configured to hold the removable particle filter 324 between the inlet end cap 327 and the core plug 322. In embodiments, the core plug holder 326 may be disposed between the inlet end cap 327 and the outlet end cap 328. The inlet end cap 327 may be disposed over the removable particle filter 324.

It is contemplated that the particles may include one or more materials such as oxides, silicates, silica (sand) (such as Ottawa, Brady or Colorado Sands), ceramics (including aluminosilicates such as "CARBOLITE," "NAPLITE" or "ECONOPROP"), sintered bauxite, plastic, mineral, glass, hollow glass spheres, thermoplastic polymers, thermoset polymers, walnut shell, pits, husks, quartz, aluminum pellets, synthetic organic particles such as nylon pellets, or combinations thereof. In addition, protective and/or hardening coatings, such as resins or epoxy may be used to modify or customize the density of the particles.

The core plug 322 comprises a core plug inlet face 322a and the removable particle filter 324 is supported by the core plug inlet face 322a, extends across a majority of the core plug inlet face 322a. The filter 324 may be characterized by, for example, a pore size rating of at least about 0.45 microns, to selectively catch/pass particles in the diverted seawater according to size. The core plug inlet face 322a of the core plug 322 and the removable particle filter 324 can be oriented to directly obstruct the flow of diverted seawater such that particles collected by the removable particle filter 324 will increase fluid pressure in diverted seawater moving through the diverted seawater sampling line 200 at a constant flow rate. It is contemplated that the particles may include sand or organisms.

The removable particle filter 324 may extend across the substantial entirety of the core plug inlet face 322a. In some embodiments, it may be acceptable for the removable particle filter 324 to extend across less than the substantial entirety of the core plug inlet face 322a.

It is contemplated that the purpose of the removable particle filter 324 is to prevent the core plug 322 from being clogged by the particles in the seawater. The removable particle filter 324 may be constructed from any of a variety of conventional or yet-to-be developed filter materials and should be designed to have a filter porosity that is selected according to the size of the particles to be monitored or otherwise counted. For example, a particle filter characterized by a pore size rating of 500 microns, would be an effective filter for monitoring particles having a size of 500 microns or greater.

It is also contemplated that the removable particle filter 324 should be designed so that it can be easily removed and replaced when it becomes clogged, or at periodic intervals, before it becomes clogged, for example, at shift changes or other predefined time intervals. In embodiments, the removable particle filter 324 may be a removable filter cartridge configured to be removed from the core plug assembly 320. For example, the removable filter cartridge may be removed and/or replaced when needed. In embodiments, the removable particle filter 324 is reusable. For example, the removable particle filter 324 may be a washable filter, to permit users to remove particles that have accumulated in the filter 324.

For example, large particles may be filtered by the removable particle filter 324 and prevent the core plug 322 from being blocked. On the other hand, the filtered particles may clog the removable particle filter 324 which may increase the pressure in diverted seawater. By replacing the removable particle filter 324 the pressure may be lowered. It is contemplated that the removable particle filter 324 may be constructed from porous materials such as paper, cloth, or the like.

The inlet pressure monitoring station 340 generates a particles count signal based on fluid pressure in diverted seawater moving through the diverted seawater sampling line 200 in the direction of the core plug inlet face 322a and the removable particle filter 324. In embodiments, the inlet pressure monitoring station 340 may comprise a pressure gauge 342 (e.g., a simple pressure gauge, a pressure transducer, or the like) coupled to the diverted seawater sampling line 200 measuring the fluid pressure in diverted seawater upstream of the core plug assembly 320.

In embodiments, the inlet pressure monitoring station 340 may generate graphical data based on the generated particles count signal. (e.g., FIG. 2) For example, the graphical data may be a chart, a graph, a diagram, or a combination thereof. In embodiments, the inlet pressure monitoring station 340 may comprise a display displaying the graphical data. For example, the display may be a monitor, a screen, or the like. The inlet pressure monitoring station 340 may include an input device, such as a microphone, a camera, a touch screen keypad, a keyboard, or a combination thereof.

In embodiments, the inlet pressure monitoring station 340 may generate an alarm based on the generated particles count signal. The inlet pressure monitoring station 340 may include an output device, such as an audio output device (e.g., a speaker, a buzzer, or the like). The alarm may be generated based on the particles count signal in the diverted seawater sampling line 200. In embodiments, the alarm may be generated when the fluid pressure in the diverted seawater sampling line 200 is greater than a certain threshold fluid pressure based on the operation requirements of the seawater injection system 10. For example, the threshold fluid pressure in the diverted seawater sampling line 200 may be between 20 psi and 400 psi.

In embodiments, the online particles count monitoring system 300 may include a relief valve 350 coupled to the diverted seawater sampling line 200. In embodiments, the relief valve 350 may further include an internal flow path coupled to the diverted seawater sampling line 200 at an upstream side. The relief valve 350 may be further fluidly coupled to a discharge line 352 coupled to the internal flow path at a downstream side. For example, when the relief valve 350 is open, the diverted seawater may be directed to the discharge line 352 to be discharged from the seawater injection system 10.

The online particles count monitoring system 300 may further comprise a relief valve controller controlling the relief valve 350. In embodiments, the inlet pressure monitoring station 340 may provide the particles count signal to an input of the relief valve controller. In embodiments, the relief valve 350 is set to open when the fluid pressure in the diverted seawater sampling line 200 exceeds a certain threshold fluid pressure based on the operation requirements of the seawater injection system 10. For example, the threshold fluid pressure may be between 20 psi and 400 psi.

In embodiments, the online particles count monitoring system 300 may comprise a seawater supply line controller controlling the primary flow of seawater moving through the primary seawater supply line 100. The inlet pressure monitoring station 340 may provide the generated particles count signal to an input of the seawater supply line controller.

Now, an online method of monitoring particle count in the seawater injection system 10 will be described. The seawater injection system 10 may be any of the seawater injection systems previously described. The online method includes steps of diverting a portion of a primary flow of seawater moving in a downstream direction through the primary seawater supply line 100 to the online particles count monitoring system 300 through the diverted seawater sampling line 200. The method further includes maintaining a constant flow rate in the diverted seawater sampling line 200 such that particles collected by the removable particle filter 324 will increase fluid pressure in diverted seawater moving through the diverted seawater sampling line 200. The method further includes generating, by the inlet pressure monitoring station 340, a particles count signal based on fluid pressure in diverted seawater moving downstream through the diverted seawater sampling line 200 in the direction of the core plug inlet face 322a and the removable particle filter 324.

Figure 2:
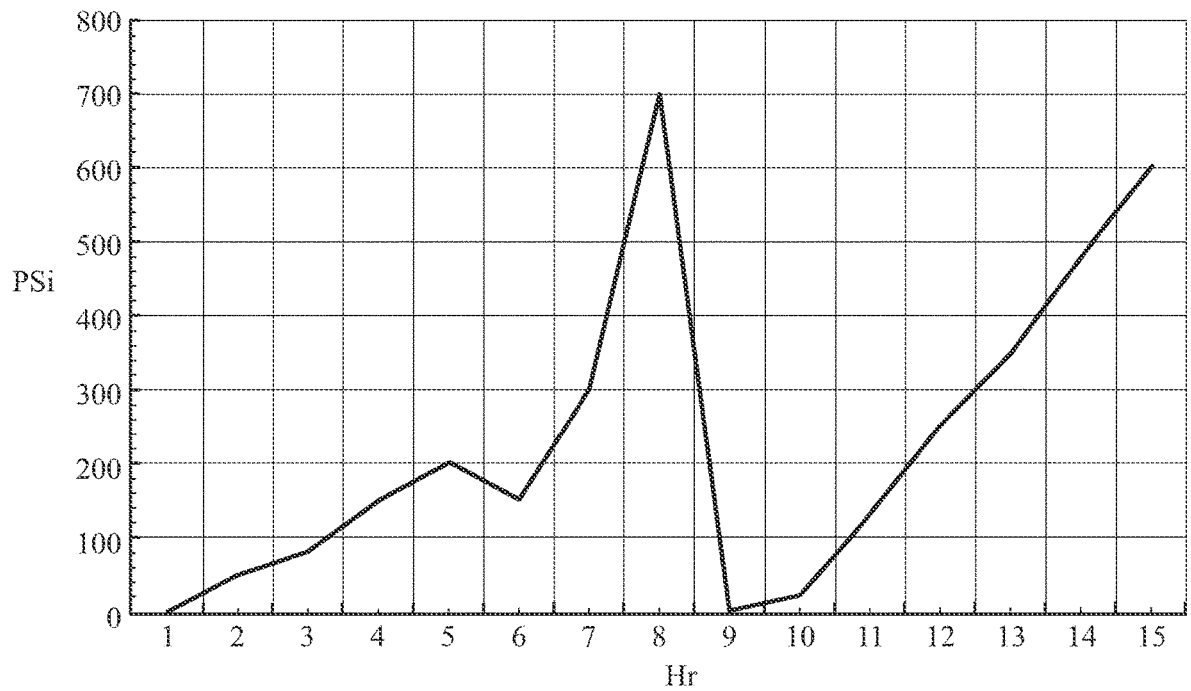
FIG. 2 graphically illustrates the relationship between a fluid pressure in diverted seawater moving through a diverted seawater sampling line and time, according to one or more embodiments herein.

Referring to FIG. 2, the relationship between a fluid pressure in diverted seawater moving through the diverted seawater sampling line 200 and time of exemplary embodiments is illustrated. The fluid pressure increases over time due to accumulated particles in the removable particle filter 324. An alarm may be generated by the inlet pressure monitoring station 340 at a threshold value. For example, the threshold fluid pressure value may be 500 psi. Based on the generated alarm, the removable particle filter 324 may be replaced. For example, an operator may replace the removable particle filter 324. The increasing fluid pressure in the diverted seawater sampling line 200 may indicate other issues different from the issues from the accumulated particles.

In case the removable particle filter 324 is not replaced, fluid pressure in the diverted seawater sampling line 200 may increase due to further accumulation of particles in the removable particle filter 324. In case the increasing pressure is not originated from the accumulated particles, fluid pressure in the diverted seawater sampling line 200 may increase even after the removable particle filter 324 is replaced. In either case, the fluid pressure in the diverted seawater sampling line 200 may keep increase. In embodiments, the relief valve controller may open the relief valve 350 based on the particles count signal indicating that fluid pressure in the diverted seawater sampling line 200 exceeds 700 psi. In embodiments, the relief valve 350 may automatically open when fluid pressure in the diverted seawater sampling line 200 exceeds 700 psi. Fluid pressure in the diverted seawater sampling line 200 may increase again after the above described pressure relief measures took place.

It is noted that recitations herein of a component of the present disclosure being "configured" in a particular way, to embody a particular property, or to function in a particular manner, are structural recitations, as opposed to recitations of intended use. More specifically, the references herein to the manner in which a component is "configured" denotes an existing physical condition of the component and, as such, is to be taken as a definite recitation of the structural characteristics of the component.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it is noted that the various details disclosed herein should not be taken to imply that these details relate to elements that are essential components of the various embodiments described herein, even in cases where a particular element is illustrated in each of the drawings that accompany the present description. Further, it will be apparent that modifications and variations are possible without departing from the scope of the present disclosure, including, but not limited to, embodiments defined in the appended claims. More specifically, although some aspects of the present disclosure are identified herein as preferred or particularly advantageous, it is contemplated that the present disclosure is not necessarily limited to these aspects.

It is noted that one or more of the following claims utilize the term "wherein" as a transitional phrase. For the purposes of defining the present invention, it is noted that this term is introduced in the claims as an open-ended transitional phrase that is used to introduce a recitation of a series of characteristics of the structure and should be interpreted in like manner as the more commonly used open-ended preamble term "comprising."

What is claimed is:

1. A seawater injection system comprising a primary seawater supply line, a diverted seawater sampling line, and an online particles count monitoring system, wherein:
   the online particles count monitoring system is fluidly coupled to the primary seawater supply line through the diverted seawater sampling line to divert a portion of a primary flow of seawater moving in a downstream direction through the primary seawater supply line to the online particles count monitoring system through the diverted seawater sampling line;
   the online particles count monitoring system comprises a diverted seawater inlet, a core plug assembly downstream of the diverted seawater inlet, a diverted seawater outlet downstream of the core plug assembly, and an inlet pressure monitoring station upstream of the core plug assembly and downstream of the diverted seawater inlet;
   the core plug assembly comprises a core plug and a removable particle filter arranged upstream of the core plug;
   the diverted seawater inlet is fluidly coupled to the diverted seawater outlet through the core plug assembly to divert seawater moving in a downstream direction through the diverted seawater inlet to the diverted seawater outlet through the removable particle filter and the core plug of the core plug assembly;
   the core plug comprises a core plug inlet face and the removable particle filter is supported by the core plug inlet face, extends across a majority of the core plug inlet face, and is characterized by a pore size rating of at least about 0.45 microns;
   the core plug inlet face and the removable particle filter are oriented to directly obstruct the flow of diverted seawater such that particles collected by the removable particle filter will increase fluid pressure in diverted seawater moving through the diverted seawater sampling line at a constant flow rate; and
   the inlet pressure monitoring station generates a particles count signal based on fluid pressure in diverted seawater moving through the diverted seawater sampling line in a downstream direction of the core plug inlet face and the removable particle filter.

2. The seawater injection system of claim 1, wherein the inlet pressure monitoring station comprises a pressure gauge coupled to the diverted seawater sampling line measuring the fluid pressure in diverted seawater upstream of the core plug assembly.

3. The seawater injection system of claim 1, wherein the inlet pressure monitoring station generates graphical data based on the generated particles count signal.

4. The seawater injection system of claim 3, wherein the inlet pressure monitoring station comprises a display displaying the graphical data.

5. The seawater injection system of claim 1, wherein the inlet pressure monitoring station generates an alarm based on the generated particles count signal.

6. The seawater injection system of claim 5, wherein the alarm is generated when the fluid pressure in the diverted seawater sampling line is greater than 20 psi.

7. The seawater injection system of claim 1, wherein:
   the online particles count monitoring system comprises a seawater supply line controller controlling the primary flow of seawater moving through the primary seawater supply line; and
   the inlet pressure monitoring station provides the generated particles count signal to an input of the seawater supply line controller.

8. The seawater injection system of claim 1, wherein the online particles count monitoring system comprises a relief valve coupled to the diverted seawater sampling line.

9. The seawater injection system of claim 8, wherein:
   the online particles count monitoring system comprises a relief valve controller controlling the relief valve; and
   the inlet pressure monitoring station provides the particles count signal to an input of the relief valve controller.

10. The seawater injection system of claim 8, wherein the relief valve is set to open when fluid pressure in the diverted seawater sampling line exceeds approximately 20 psi.

11. The seawater injection system of claim 1, wherein the diverted seawater sampling line is configured such that no more than approximately 5% of the primary flow of seawater is diverted from the primary seawater supply line.

12. The seawater injection system of claim 1, wherein the removable particle filter extends across less than an entirety of the core plug inlet face.

13. The seawater injection system of claim 1, wherein the removable particle filter extends across a substantial entirety of the core plug inlet face.

14. The seawater injection system of claim 1, wherein the removable particle filter is a removable filter cartridge configured to be removed from the core plug assembly.

15. The seawater injection system of claim 1, wherein:
the core plug assembly further comprises a core plug holder, an inlet end cap coupled to the diverted seawater inlet, and an outlet end cap coupled to the diverted seawater outlet; and
the core plug holder and the inlet end cap are collectively configured to hold the removable particle filter between the inlet end cap and the core plug.

16. The seawater injection system of claim 15, wherein the core plug is disposed between the inlet end cap and the outlet end cap, and the inlet end cap is disposed over the removable particle filter.

17. The seawater injection system of claim 1, wherein the seawater injection system further comprises a diverted seawater sampling line controller that controls the diverted seawater sampling line to maintain the constant flow rate in the diverted seawater sampling line.

18. The seawater injection system of claim 17, wherein the diverted seawater sampling line controller further controls the diverted seawater sampling line to open and close.

19. An online particles count monitoring system comprising:
a diverted seawater inlet;
a core plug assembly downstream of the diverted seawater inlet, the core plug assembly comprising a core plug and a removable particle filter arranged upstream of the core plug;
a diverted seawater outlet downstream of the core plug assembly; and
an inlet pressure monitoring station upstream of the core plug assembly and downstream of the diverted seawater inlet, wherein:
the diverted seawater inlet is fluidly coupled to the diverted seawater outlet through the core plug assembly to divert seawater moving in a downstream direction through the diverted seawater inlet to the diverted seawater outlet through the removable particle filter and the core plug of the core plug assembly;
the core plug comprises a core plug inlet face and the removable particle filter is supported by the core plug inlet face, extends across a majority of the core plug inlet face, and is characterized by a pore size rating of at least about 0.45 microns;
the core plug inlet face of the core plug and the removable particle filter are oriented to directly obstruct the flow of diverted seawater such that particles collected by the removable particle filter will increase fluid pressure in diverted seawater moving through a diverted seawater sampling line that is fluidly coupled to the online particles count monitoring system, at a constant flow rate; and
the inlet pressure monitoring station generates a particles count signal based on fluid pressure in diverted seawater moving through the diverted seawater sampling line that is fluidly coupled to the online particles count monitoring system, in a downstream direction of the core plug inlet face and the removable particle filter.

20. An online method of monitoring particle count in a seawater injection system comprising a primary seawater supply line, a diverted seawater sampling line, and an online particles count monitoring system, wherein:
the online particles count monitoring system is fluidly coupled to the primary seawater supply line through the diverted seawater sampling line;
the online particles count monitoring system comprises a diverted seawater inlet, a core plug assembly downstream of the diverted seawater inlet, a diverted seawater outlet downstream of the core plug assembly, and an inlet pressure monitoring station upstream of the core plug assembly and downstream of the diverted seawater inlet;
the core plug assembly comprises a core plug and a removable particle filter arranged upstream of the core plug;
the diverted seawater inlet is fluidly coupled to the diverted seawater outlet through the core plug assembly to divert seawater moving in a downstream direction through the diverted seawater inlet to the diverted seawater outlet through the removable particle filter and the core plug of the core plug assembly;
the core plug comprises a core plug inlet face and the removable particle filter is supported by the core plug inlet face, extends across a majority of the core plug inlet face, and is characterized by a pore size rating of at least about 0.45 microns;
the core plug inlet face of the core plug and the removable particle filter are oriented to directly obstruct the flow of diverted seawater; and
the online method comprises:
diverting a portion of a primary flow of seawater moving in a downstream direction through the primary seawater supply line to the online particles count monitoring system through the diverted seawater sampling line;
maintaining a constant flow rate in the diverted seawater sampling line such that particles collected by the removable particle filter will increase fluid pressure in diverted seawater moving through the diverted seawater sampling line; and
generating, by the inlet pressure monitoring station, a particles count signal based on fluid pressure in diverted seawater moving downstream through the diverted seawater sampling line in a downstream direction of the core plug inlet face and the removable particle filter.

* * * * *